(12) United States Patent
Mao et al.

(10) Patent No.: US 12,089,619 B2
(45) Date of Patent: Sep. 17, 2024

(54) SACCHAROPOLYSPORA COMPOSITION AND ITS APPLICATION IN FOODS

(71) Applicants: Jiangnan University, Wuxi (CN); Jiangnan University (Shaoxing) Industrial Technology Research Institute, Shaoxing (CN)

(72) Inventors: Jian Mao, Wuxi (CN); Shuangping Liu, Wuxi (CN); Zhilei Zhou, Wuxi (CN); Zhongwei Ji, Wuxi (CN); Xiao Han, Wuxi (CN)

(73) Assignees: JIANGNAN UNIVERSITY, Wuxi (CN); JIANGNAN UNIVERSITY (SHAOXING) INDUSTRIAL TECHNOLOGY RESEARCH INSTITUTE, Shaoxing (CN)

( * ) Notice: Subject to any disclaimer, the term of this patent is extended or adjusted under 35 U.S.C. 154(b) by 0 days.

(21) Appl. No.: 17/720,375

(22) Filed: Apr. 14, 2022

(65) Prior Publication Data
US 2022/0322714 A1   Oct. 13, 2022

Related U.S. Application Data

(63) Continuation of application No. PCT/CN2021/077377, filed on Feb. 23, 2021.

(30) Foreign Application Priority Data

Aug. 13, 2020 (CN) .......................... 202010812161.6
Aug. 13, 2020 (CN) .......................... 202010812299.6

(51) Int. Cl.
A23L 27/24     (2016.01)
A23L 17/10     (2016.01)
(Continued)

(52) U.S. Cl.
CPC ............... *A23L 27/24* (2016.08); *A23L 17/10* (2016.08); *A23L 27/50* (2016.08); *C12G 3/022* (2019.02); *C12J 1/04* (2013.01); *C12N 1/20* (2013.01)

(58) Field of Classification Search
CPC .......... A23L 27/24; A23L 17/10; A23L 27/50; C12G 3/022; C12J 1/04; C12N 1/20
(Continued)

(56) References Cited

FOREIGN PATENT DOCUMENTS

CN     110914425 A     3/2020
CN     111961615 A     11/2020
(Continued)

OTHER PUBLICATIONS

Lacey et al. A novel actinomycete from sugar-cane Bagasse: *Saccharopolyspora hirsuta* gen. et sp. nov., Journal of General Microbiology (1975), 88,75-85.*

*Primary Examiner* — Donald R Spamer
*Assistant Examiner* — Philip A Dubois
(74) *Attorney, Agent, or Firm* — IPRO, PLLC

(57) ABSTRACT

The disclosure discloses a *Saccharopolyspora* composition and its application in foods, and belongs to the technical field of food fermentation. The disclosure screens *Saccharopolyspora hirsuta* J2 and *Saccharopolyspora jiangxiensis* J3 that have an effect of reducing biogenic amine content from wheat koji, and the two strains are prepared into a *Saccharopolyspora* mixed preparation for use in a preparation process of a fermented alcoholic beverage, fermented food or fermented condiment, so that amino acid content and nutritional value of a fermented product can be improved while the biogenic amine content is reduced, thereby achieving effects of enhancing quality of the fermented food and
(Continued)

improving safety of the fermented food, and therefore, the *Saccharopolyspora* composition has a broad application prospect.

9 Claims, 7 Drawing Sheets

Specification includes a Sequence Listing.

(51) Int. Cl.
*A23L 27/50* (2016.01)
*C12G 3/022* (2019.01)
*C12J 1/04* (2006.01)
*C12N 1/20* (2006.01)

(58) Field of Classification Search
USPC .......................................................... 426/52
See application file for complete search history.

(56) References Cited

FOREIGN PATENT DOCUMENTS

| | | |
|---|---|---|
| CN | 111979146 A | 11/2020 |
| CN | 111979148 A | 11/2020 |
| WO | 2008092950 A1 | 8/2008 |

\* cited by examiner

```
                              SEQUENCE LISTING

<160> NUMBER OF SEQ ID NOS: 4

<210> SEQ ID NO 1
<211> LENGTH: 1387
<212> TYPE: DNA
<213> ORGANISM: Saccharopolyspora hirsuta

<400> SEQUENCE: 1
gaccactccc cccacaaggg ttgggccatg ggcttcgggt gttaccgact ttcatgacgt      60
gacgggcggt gtgtacaagg cccgggaacg tattcaccgc agcaatgctg atctgcgatt     120
actagcgact ccgacttcac ggggtcgagt tgcagacccc gatccgaact gagaccggct     180
ttaagggatt cgctcaacct cacgatctcg cagccctctg taccggccat tgtagcatgt     240
gtgaagcccc gggcataagg ggcatgatga cttgacgtca tccccacctt cctccgagtt     300
gaccccggca gtcccccacg agtccccggc attacccgct ggcaacatag ggcaagggtt     360
gcgctcgttg cgggacttaa cccaacatct cacgacacga gctgacgaca gccatgcacc     420
acctgtacac caaccacaag ggaaaccccc tctcagggc tgtctagtgc atgtcaaacc     480
caggtaaggt tcttcgcgtt gcatcgaatt aatccacatg ctccgccgct tgtgcgggcc     540
cccgtcaatt cctttgagtt ttagccttgc ggccgtactc cccaggcggg gcgcttaatg     600
cgttagctac ggcacggaaa cagtggaacc catcccaca cctagcgccc aacgtttacg     660
gcgtggacta ccagggtatc taatcctgtt cgctcccac gctttcgctc ctcagcgtca     720
gtatcggccc agagacccgc cttcgccacc ggtgttcctc ctgatatctg cgcatttcac     780
cgctacacca ggaattccag tctcccctac cgaactcaag tctgcccgta tccaccgcaa     840
gccaggagtt aagctcccgg ttttcacgat agacgcgaca aaccgcctac gagctcttta     900
cgcccaataa atccggacaa cgctcgcacc ctacgtatta ccgcggctgc tggcacgtag     960
ttagccggtg cttcttctac acctaccgtc acccgaaggc ttcgtcgatg tcgaaagagg    1020
tttacaaccc gaaggccgtc atccccacg cggcgttgct gcgtcaggct ttcgcccatt    1080
gcgcaagatt ccccactgct gcctcccgta ggagtctggg ccgtgtctca gtcccagtgt    1140
ggccggtcac cctctcaggc cggctacccg tcgtcgcctt ggtaggccac tacccccacca    1200 acaagctgat aggccgcggg ctcatcctgc accgccagaa cttcccacac cagaacatgc    1260
ctccaggtgt cgtatccggt attagacctc gtttccaagg cttatcccga agtgcagggc    1320
agattaccca cgtgttactc acccgttcgc cactcatcca cacccgaaag tgcttcagcg    1380
ttcgact                                                              1387

<210> SEQ ID NO 2
<211> LENGTH: 1370
<212> TYPE: DNA
<213> ORGANISM: Saccharopolyspora jiangxiensis

<400> SEQUENCE: 2
gggttgggcc atgggcttcg ggtgttaccg actttcatga cgtgacgggc ggtgtgtaca      60
aggcccggga acgtattcac cgcagcaatg ctgatctgcg attactagcg actccgactt    120
cacggggtcg agttgcagac cccgatccga actgagaccg gctttaaggg attcgctcaa    180
cctcacgatc tcgcagccct ctgtaccggc cattgtagca tgtgtgaagc cctgggcata    240
```

```
aggggcatga tgacttgacg tcatccccac cttcctccga gttgaccccg gcagtccccc      300
acgagtcccc ggcatcaccc gctggcaaca tagggcaagg gttgcgctcg ttgcgggact      360
taacccaaca tctcacgacc acgaagctga cgacagccat gcacctacct gtacaccaac      420
cacaaaggga aacccctct caggggctgt ctagtgcatg tcaaaccmag gtaaggttyt       480
tcgcgttgca tsgaattaat ccacatgctc cgccgcttgt gcgggccccc gtcaattcct      540
ttgagtttta gccttgcggc cgtactcccc aggcggggcg cttaatgcgt ttagctacgg      600
cacggaaaca gtggaaccca tccccacacc tagcgcccaa cgtttacggc gtggactacc      660
agggtatcta atcctgttcg ctccccacgc tttcgctcct cagcgtcagt atcggcccag      720
agacccgcct tcgccaccgg tgttcctcct gatatctgcg catttcaccg ctacaccagg      780
aattccagtc tcccctaccg aactcaagtc tgcccgtatc caccgcaagc caggagttaa      840
gctcccggtt ttcacgatag acgcgacaaa ccgcctacga gctctttacg cccaataaat      900
ccggacaacg ctcgcaccct acgtattacc gcggctgctg gcacgtagtt tagccggtgc      960
tttcttctac accttactcg tcaacccyaa aggggccttc gtcgatgtcg aaagtaggtt     1020
tacaacccga aggccgtcat cccccacgcg gcgttgctgc gtcaggcttt cgcccattgc     1080
gcaagattcc ccactgctgc ctcccgtagg agtctgggcc gtgtctcagt cccagtgtgg     1140
ccggtcaccc tctcaggccg gctaccegtc gtcgccttgg taggccatca ccccaccaac     1200
aagctgatag gccgcgggct catcctgcac cgccggaact ttccacacac gaagatgcct     1260
ccatgtgtcc tatccggtat tagacccegt ttccaaggct tatcccagag tgcagggcag     1320
attacccacg tgttactcac ccgttcgcca ctcatccaca cccgaaagtg                1370

<210> SEQ ID NO 3
<211> LENGTH: 20
<212> TYPE: DNA
<213> ORGANISM: Artificial sequence
<220> FEATURE:
<223> OTHER INFORMATION: synthetic DNA

<400> SEQUENCE: 3
agagtttgat cctggctcag                                                    20

<210> SEQ ID NO 4
<211> LENGTH: 19
<212> TYPE: DNA
<213> ORGANISM: Artificial sequence
<220> FEATURE:
<223> OTHER INFORMATION: Synthetic DAN

<400> SEQUENCE: 4
ggttaccttg ttacgactt                                                     19
```

SACCHAROPOLYSPORA COMPOSITION AND ITS APPLICATION IN FOODS

TECHNICAL FIELD

The disclosure herein relates to a *Saccharopolyspora* composition and its application in foods, and belongs to the technical field of food fermentation.

BACKGROUND

Huangjiu is brewed wine, which is generally made from glutinous rice, corn and husked millet as raw materials, by adding wheat koji and *Saccharomyces cerevisiae* as a saccharifying agent and a starter, through cooking, koji adding, saccharification and fermentation, pressing, filtering, sterilization, storage and blending. In addition to main components such as water and alcohol, huangjiu further contains 18 amino acids, including 8 essential amino acids. These 8 amino acids are several times more than a same amount of wine or beer, and therefore, regular consumption of huangjiu is beneficial to health. Huangjiu is rich in antioxidant substances, such as polyphenols, polysaccharides, polypeptides, etc., and therefore, it has antioxidant activity. Different from beer and wine, huangjiu is brewed by employing an open fermentation technology. Its fermentation system is rich amino acid content, its microorganisms are complex in species and large in number, and a bacterial community structure is complex. Bacteria involved in fermentation mainly include *Acetobacter aceti, Lactobacillus, Bacillus, Saccharopolyspora*, etc. However, metabolites of the microorganisms not only bring a unique flavor to huangjiu, but also make huangjiu contain some harmful substances, such as biogenic amine, etc.

Biogenic amine is a nitrogen-containing organic basic small molecule compound, formed by amino acid decarboxylation, and is commonly found in animals, plants and microorganisms. An appropriate amount of biogenic amine can promote growth, scavenge free radicals, enhance metabolic activity, and enhance immunity, and has an important physiological function in a human body. However excessive intake of the biogenic amine can cause expansion of an artery, a blood vessel and a capillary, which leads to adverse physiological reactions such as diarrhea, a headache, an abdominal spasm, vomiting, and even death. The biogenic amine is widely present in various foods, and is especially high in content in fermented foods such as yogurt, huangjiu, baijiu, cooking wine, soy sauce, vinegar and wine.

The biogenic amine in the fermented foods is mainly formed by amino acid decarboxylase produced by microbial metabolism acting on a free amino acid. In a fermentation process, the microorganisms metabolize to produce proteases and carboxypeptidases to act on a protein in grain, and the protein decomposes to produce low-molecular peptides and amino acids, which provides abundant precursor substances for production of the biogenic amine, and under the action of the amino acid decarboxylase, the biogenic amine will be massively generated.

At present, there is no report on application of *Saccharopolyspora* in food fermentation and biogenic amine reduction in domestic and foreign research. Therefore, screening microorganisms with excellent properties with the use of a modern biotechnology is of great significance for producing a high-quality and high-yield fermented food with a unique flavor, and improving the safety of the fermented food.

SUMMARY

Objectives of the disclosure are to solve the problem that biogenic amine content of a conventional brewed food is relatively high, and to provide *Saccharopolyspora* with excellent performance for application to fermentation processes of alcoholic beverages (baijiu and huangjiu), sausages and soy sauce for biological augmentation, to reduce the biogenic amine content of the fermented food, so that the taste and flavor of the food are improved, and the application of *Actinomycetes* in the conventional fermented food is better developed.

A first objective of the disclosure is to provide a *Saccharopolyspora* composition, containing *Saccharopolyspora hirsuta* J2 and *Saccharopolyspora jiangxiensis* J3.

The *S. hirsuta* J2 was deposited in the China Center for Type Culture Collection on Apr. 30, 2020, with a preservation number of CCTCC NO: M 2020103.

The *S. jiangxiensis* J3 was deposited in the China Center for Type Culture Collection on Apr. 30, 2020, Wuhan University, Wuhan, China, with a preservation number of CCTCC NO: M 2020104.

The *S. hirsuta* J2 and the *S. jiangxiensis* J3 of the disclosure both have the following excellent properties:

(1) Applied to a food fermentation system, they will not affect normal fermentation of a food.

(2) Pure wheat koji prepared from the strains is suitable for fermentation of huangjiu, and can increase the amino acid content of the huangjiu.

(3) The amount of biogenic amines produced is less than 2.5 mg/L, and the amount of biogenic amines detected is very small.

(4) They both have a degradation effect on tyramine, histamine, putrescine and cadaverine.

(5) They are applicable to sausage, huangjiu, baijiu, cheese and soy sauce fermentation, and are capable of reducing the biogenic amines.

A second objective of the disclosure is to provide a microbial preparation containing the *Saccharopolyspora* composition.

In an embodiment, the number of *Saccharopolyspora* per gram or per milliliter of starter is greater than or equal to $1 \times 10^6$ CFU.

In an embodiment, the microbial preparation is a starter containing *Saccharopolyspora* cells that is obtained by inoculating the *Saccharopolyspora* into an *Actinomycetes* liquid medium and culturing the *Saccharopolyspora* at 28-30° C.

A third objective of the disclosure is to provide koji prepared by applying the *Saccharopolyspora* composition, and its preparation method includes: raw materials are crushed, the crushed raw materials are stirred with water, the stirred raw materials are sterilized, a strain is inoculated in a sterile environment, with an inoculum size of 5%0-15%, and a cell concentration of $10^5$-$10^8$ CFU/mL, the strain is cultured at 25-55° C. for 72-96 h, and after the culture ends, the cultured strain is preserved for later use.

In an embodiment, raw materials of the *Saccharopolyspora* koji are spread for cooling under a sterile condition after cooking; a well mixing process of the inoculated koji and the raw materials and a subsequent rake-stirring process are both performed in the sterile environment; the *Saccharopolyspora* koji is obtained by inoculation and culture in the sterile environment.

In an embodiment, the koji is mixed wheat koji obtained by mixing pure wheat koji prepared from the *S. hirsuta* J2 and pure wheat koji prepared from the *S. jiangxiensis* J3.

In an embodiment, the method for preparing wheat koji includes the following steps:

(1) Wheat grinding: A degree of crushing of wheat is 3-5 pieces per grain, with a small amount of powder, and a wheat grain structure is made to broken and starch is exposed.

(2) Wheat tempering: 30-40% of clear water is added into the material obtained after treatment in step (1) based on the mass of the material, and stirring is performed for 15-25 min to make it fully and evenly absorb moisture.

(3) Cooking for sterilization: The material obtained after treatment in step (2) is cooked for sterilization.

(4) Inoculation: After the material obtained in step (3) is cooled to be below 40° C., activated S. hirsuta J2 is inoculated with an inoculum concentration of $10^5$-$10^6$ CFU/mL.

(5) Fermentation.

In an embodiment, the method in step (5) includes the following steps:

a) In a spore germination period, 6 hours after a koji material enters a tray, a sample temperature slowly rises to about 34-35° C., an automatic control mode starts small-air volume intermittent ventilation, for 5-10 minutes each time, at an interval of 2 hours, the sample temperature is made to drop to 32° C., and it is required that the koji material is blown through evenly.

b) In a mycelium growth period, after 3-5 times of intermittent ventilation, mycelia start to grow, the sample temperature rises to 35° C. or above, the koji material starts to agglomerate, and at this time, continuous ventilation should be performed to maintain the sample temperature at 35±2° C.

c) In a mycelium propagation period, 12 hours after inoculation, the sample temperature rises rapidly, and at this time, koji turning should be performed depending on a first-time agglomeration situation; before the koji turning, a temperature measurement probe is raised first, a koji turning machine is enabled, then the koji material is spread, the temperature measurement probe is put down, and a ventilation and spraying system is enabled.

d) After the first-time koji turning, the sample temperature is kept between 36-37° C., ventilation and spraying are kept smooth, and about 20 hours later, the koji material agglomerates again, it is observed by naked eyes that the koji material looks white, the temperature is controlled at 37° C. or below, second-time koji turning is performed, and after the second-time koji turning, the sample temperature should be controlled at 35±2° C.

A fourth objective of the disclosure is to provide application of the mixed wheat koji in huangjiu fermentation.

A fifth objective of the disclosure is to provide application of the mixed wheat koji in preparation of a fermented food, beverage or condiment.

In an embodiment, the food includes, but is not limited to, a fermented or semi-fermented food of a sausage.

In an embodiment, the beverage includes, but is not limited to, fermented huangjiu or baijiu.

In an embodiment, the condiment includes, but is not limited to, soy sauce or sausage.

In an embodiment, the application is to carry out fermentation after the mixed wheat koji and wine brewing raw materials are mixed.

In an embodiment, the method is to perform fermentation after pure wheat koji is mixed with raw materials such as rice, distiller's yeast, etc. with an inoculum size of 12-16% in a fermentation tank, and a conventional fermentation technology is employed during fermentation.

A sixth objective of the disclosure is to provide application of the Saccharopolyspora composition or mixed wheat koji in reducing biogenic amines in a sausage, huangjiu, baijiu, soy sauce, and cheese.

In an embodiment, the biogenic amine includes, but is not limited to, tyramine, histamine, putrescine and cadaverine.

In an embodiment, the brewed huangjiu and baijiu are made by preparing pure koji from the Saccharopolyspora first, and adding the pure koji into an alcoholic fermentation.

The disclosure has the following beneficial effects:

(1) Applied to a food fermentation system, the strain of the disclosure will not affect normal fermentation of foods.

(2) The pure wheat koji prepared from the S. hirsuta J2 can be used for huangjiu fermentation, which not only can promote an alcohol yield but also can increase amino acid content of the huangjiu. The highest amino acid content of pure fermented huangjiu reaches 6434.81±123.3 mg/L, and is increased by 40.37% in comparison with that of samples in a control group. Moreover, addition of the strain has no obvious effect on a conventional huangjiu flavor. The biogenic amine content of a sample group added with the S. hirsuta J2 is reduced by 21.71% in comparison with that in the control group, and at the same time, the amino acid content and nutritional value of the huangjiu are improved, thereby achieving objectives of increasing the amino acid content and volatile substance content of the huangjiu and promoting quality of the huangjiu.

(3) The amount of biogenic amines produced by S. hirsuta J2 is less than 2.5 mg/L, the amount of biogenic amines detected is very small, and the biogenic amines are basically not produced. A degradation rate to the tyramine, a degradation rate to the histamine, a degradation rate to the putrescine, a degradation rate to the cadaverine and a degradation rate to total biogenic amines by the S. hirsuta J2 reach 77.41%, 100%, 58.1%, 47.71% and 72.98%, respectively, and therefore, the S. hirsuta J2 is very capable of reducing the biogenic amines.

(4) Meanwhile, the Saccharopolyspora has an effect of reducing the biogenic amines in the fermented foods. When it is applied to sausage fermentation, average content of the biogenic amines in the sausage fermented with the S. hirsuta J2 is 129.60 mg/kg, and is reduced by 36.19% in comparison with that in the control group, which shows a significant effect of reducing the biogenic amines. Biogenic amine content of baijiu added with the S. hirsuta J2 is reduced by 24.32% in comparison with that in the control group. Biogenic amine content of soy sauce added with the S. hirsuta J2 is reduced by 34.28% in comparison with that in the control group. Biogenic amine content of cheese added with the S. hirsuta J2 is reduced by 16.37% in comparison with that in the control group.

(5) The S. hirsuta J2 has effects of improving quality and reducing harm. When it is applied to cigarette fermentation, harmful component content, i.e. tar content, HCN content, phenol content, $NH_3$ content and nitrite content of fermented tobacco added with the S. hirsuta J2 is reduced by 23.51%, 16.25%, 19.75%, 27.09% and 37.62%, respectively in comparison with those in the control group.

(6) The S. hirsuta J2 has an effect of increasing a nutrient conversion rate. When it is applied to feed fermentation, organic acid content, amino acid content and crude protein content of the fermented feed added with the S. hirsuta J2 are increased by 26.77%, 21.98%, and 18.53%, respectively.

The disclosure further provides a mixed bacteria preparation containing the S. hirsuta J2 and the S. jiangxiensis J3, and the mixed bacteria preparation has the following uses:

(1) The amino acid content of the huangjiu fermented with the *Saccharopolyspora* mixed bacteria preparation is highest. Addition of the strain has no obvious effect on a conventional huangjiu flavor. Biogenic amine content is reduced by 42.17% in comparison with that in the control group, and amino acid content and nutritional value of the huangjiu are improved, thereby achieving the objectives of increasing the amino acid content and volatile substance content of the huangjiu and promoting the quality of the huangjiu.

(2) The *Saccharopolyspora* mixed bacteria preparation has an effect of reducing the biogenic amines. The biogenic amine content of a stinky mandarin fish added with the mixed bacteria preparation is reduced by 20.87% in comparison with that in the control group. When the mixed bacteria preparation is used inproduction of cooking wine, biogenic amine content of the cooking wine can be reduced by 23.16% in comparison with that in the control group. When the mixed bacteria preparation is used in production of vinegar, biogenic amine content of the vinegar can be reduced by 25.08% in comparison with that in the control group. When the mixed bacteria preparation is used in production of cheese, biogenic amine content of the cheese can be reduced by 13.33% in comparison with that in the control group.

(3) The *Saccharopolyspora* mixed bacteria preparation has effects of improving quality and reducing harm. When it is applied to cigarette fermentation, the harmful component content, i.e. the tar content, the HCN content, the phenol content, the $NH_3$ content and the nitrite content of the fermented tobacco added with the mixed bacteria preparation is reduced by 30.12%, 17.14%, 22.01%, 16.73% and 27.15%, respectively, in comparison with those in the control group.

(4) The *Saccharopolyspora* mixed bacteria preparation has an effect of improving a nutrient conversion rate. When it is applied to feed fermentation, the organic acid content, the amino acid content and the crude protein content of the fermented feed added with the mixed bacteria preparation are increased by 29.18%, 10.22% and 14.48%, respectively, in comparison with those in the control group.

Biological Material Deposit

*Saccharopolyspora jiangxiensis* is classified and named as *Saccharopolyspora jiangxiensis* J3, and was deposited in the China Center for Type Culture Collection, Wuhan University, Wuhan, China, on Apr. 30, 2020, with a preservation number of CCTCC NO: M 2020104.

*Saccharopolyspora hirsuta* is classified and named as *Saccharopolyspora hirsuta* J2, and was deposited in the China Center for Type Culture Collection, Wuhan University, Wuhan, China, on Apr. 30, 2020, with a preservation number of CCTCC NO: M 2020103.

DETAILED DESCRIPTION

Figure 1:
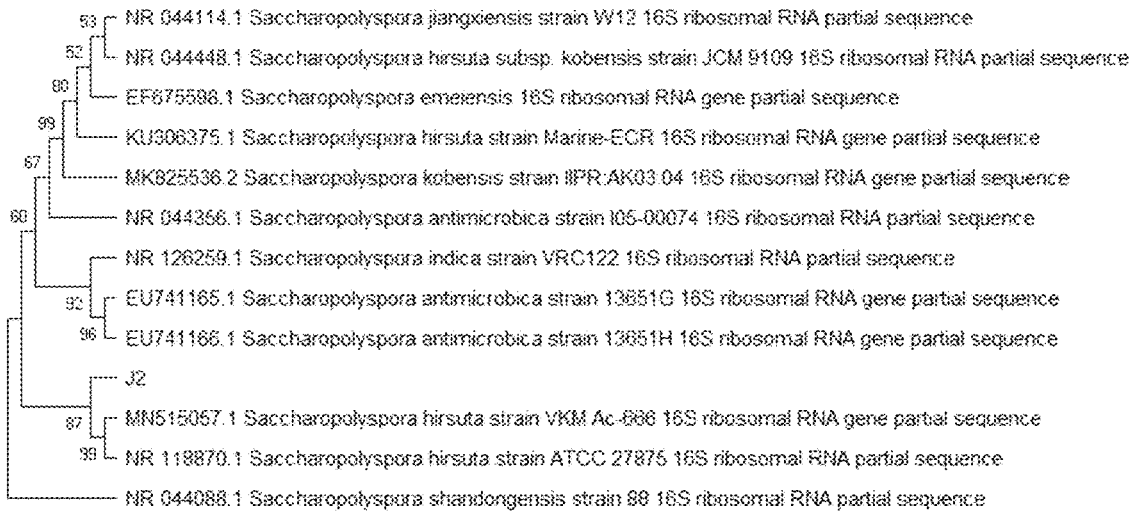
FIG. 1 is a phylogenetic tree of *S. hirsuta* J2.

Detection of physical and chemical indexes of huangjiu: Alcoholic content, amino acid nitrogen and total acid are determined in accordance with GB/T 13662-2018. Biogenic amine content and flavor substances are detected by high performance liquid chromatography (HPLC) and a gas chromatography-mass spectrometer (GC-MS). Reducing sugar content is determined by employing a DNS method.

Detection of physical and chemical indexes of a sausage: Crude protein content is determined in accordance with a GB5009.3-2010 semi-micro Kjeldahl method; moisture content is determined in accordance with a GB/T 9695.15-2008 method. pH determination includes: 10 g of a sample is taken, 90 mL of distilled water is added for homogenization, then the mixture stands for 2 min, and a pH value of a supernatant is determined with a pH meter.

Determination method of biogenic amine content: 1 mL of a to-be measured solution is accurately measured and placed into a 15 mL centrifuge tube. 1 mL of a saturated $NaHCO_3$ solution is added. Well mixing is performed. 2 mL of a dansyl chloride (5 mg/mL acetone) reagent is added. After well mixing, the mixture is put in a 65° C. thermostat water bath for dark derivation for 30 min. After standing at room temperature, 0.5 mL of a saturated NaCl solution is added. After well mixing, 5 mL of ethyl ether is added. Vortex shaking is performed for 20 s. After standing for stratification, an upper organic phase is transferred into a 15 mL centrifuge tube, a lower aqueous phase is extracted again, two extracts are combined, and blow-drying with nitrogen is performed in a 50° C. water bath. 1 mL of acetonitrile is added and shaken and mixed well to dissolve residues. The dissolved solution passes through a 0.22 μm filter membrane. Determination is performed by the high performance liquid chromatography (HPLC).

Example 1: Screening and Identification of *Saccharopolyspora*

(1) Collection and Pretreatment of Samples

Wheat koji samples were collected from a huangjiu factory in Shaoxing City, Zhejiang Province, and the collected wheat koji was stored in a sealed sterile plastic bag at 4° C. 5 g of wheat koji was weighed and placed into a 50 mL centrifuge tube, 30 mL of distilled water was added, and the 50 mL centrifuge tube was put in a 30° C. shake incubator to culture the wheat koji for 30 min.

(2) Plate Screening of Strains

*Actinomycetes* screening medium: Potassium nitrate 1.0 g/L, potassium dihydrogen phosphate 0.5 g/L, magnesium sulfate 0.5 g/L, ferrous sulfate 0.01 g/L, sodium chloride 0.5 g/L, soluble starch 20.0 g/L, and agar 15.0 g/L; pH 7.2-7.4 (25° C.).

In a sterile operating environment, 1 mL of a sample was drawn with a sterile pipette and placed in a 15 mL sterile centrifuge tube. Sterile water was added to 10 mL. Well mixing was performed to prepare a $10^{-1}$ sample homogenate. 1 mL of the $10^{-1}$ sample homogenate was drawn with the sterile pipette and placed into a 15 mL sterile centrifuge tube. Sterile water was added to 10 mL. Well mixing was performed to prepare a $10^{-2}$ sample homogenate. According to the above operations, $10^{-1}$-$10^{-6}$ ten-fold increasing series of diluted homogenates of wheat koji, rice milk and fermented mash were prepared.

100 μL of each dilution of bacterial solutions of the wheat koji, fermented mash, and rice milk were drawn, spread on the *Actinomycetes* screening medium, and cultured at 28° C. for 1-7 d. Single milky-white, thin, raised or convex and slightly wrinkled colonies were picked on a plate with a moderate colony density, and were streaked-inoculated onto the *Actinomycetes* screening medium. Streaking was repeated to determine pure colonies, and screened strains were preserved.

(3) Strain Identification

Genomes of the screened strains were extracted, and 16S rDNA amplification sequencing was performed on the screened strains.

PCR amplification primers were 27F (5'-AGAGTTT-GATCCTGGCTCAG-3') and 1492R (5'-GGTTACCTTGT-TACGACTT-3'.

PCR amplification system (50 μL): 2×Taq PCR Master Mix 25 μL, upper and lower primers both 1 μL, template 1 μL, and sterile water 22 μL added to 50 μL.

PCR amplification procedures: Pre-denaturation at 94° C. for 3 min, denaturation at 95° C. for 30 s, annealing at 58° C. for 30 s, extension at 72° C. for 2 min, a total of 35 cycles, and final extension at 72° C. for 8 min.

Figure 2:
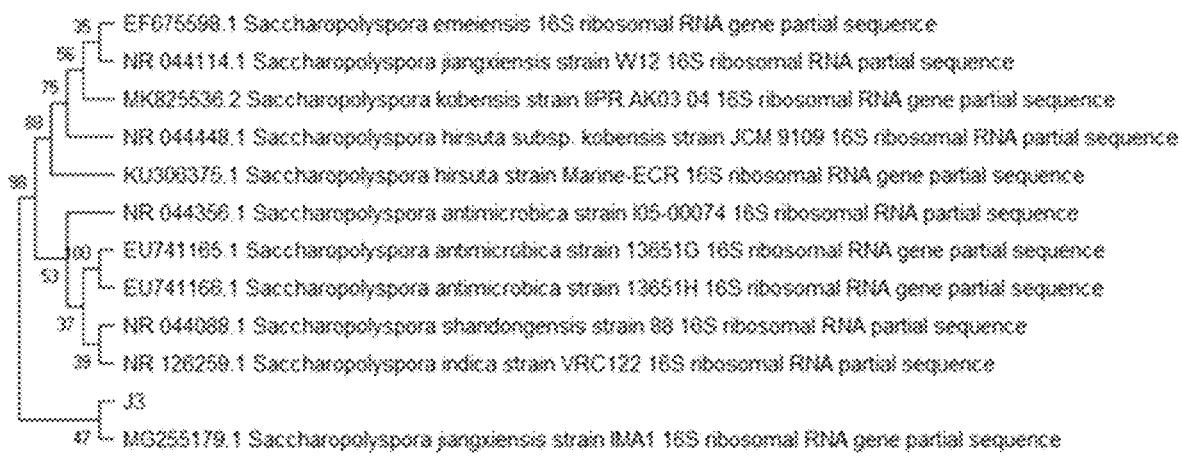
FIG. 2 is a phylogenetic tree of *S. jiangxiensis* J3.
Figure 3A:
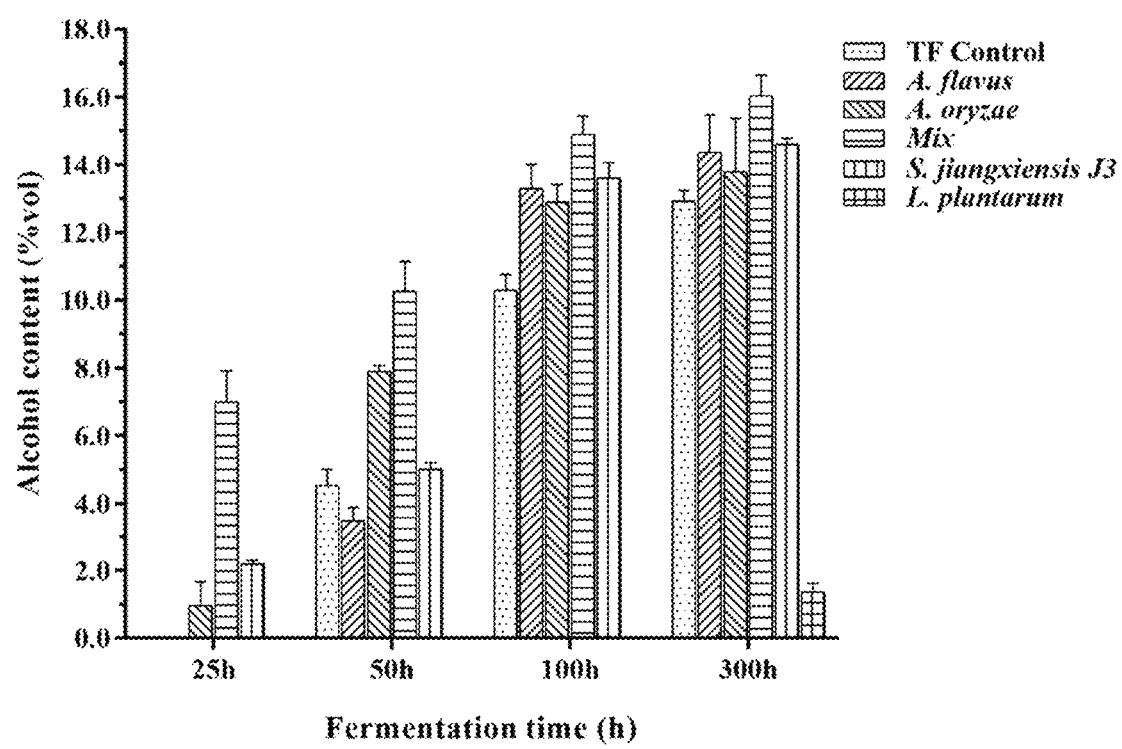
FIG. 3A is a change in alcoholic content in a huangjiu fermentation process.
Figure 3B:
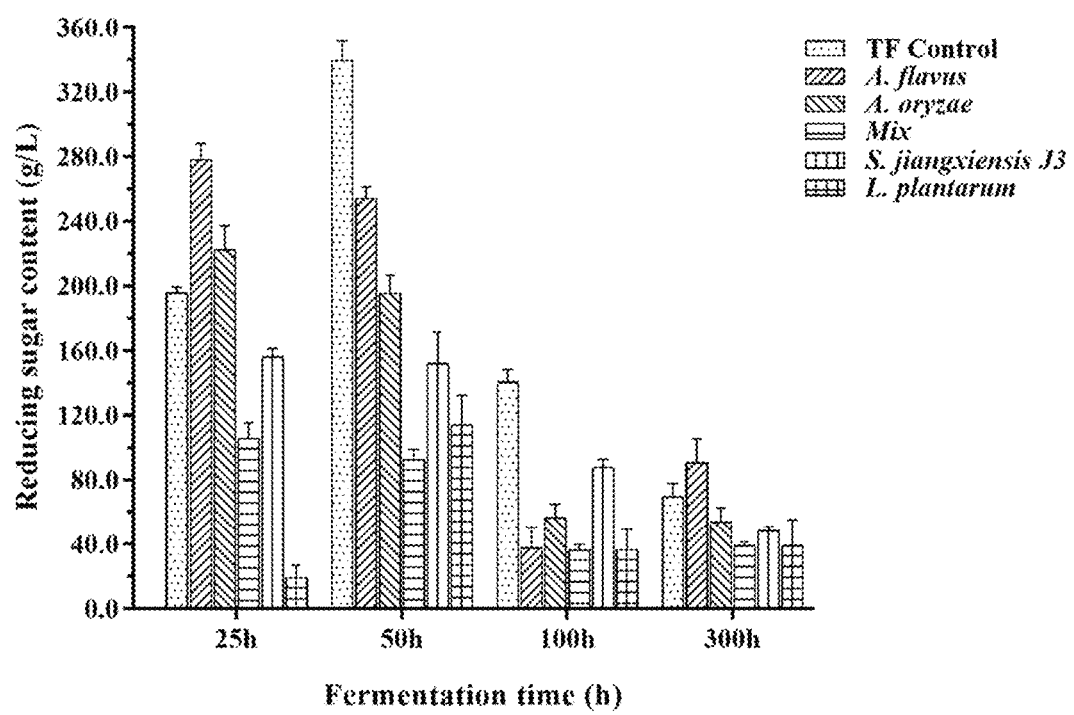
FIG. 3B is a change of reducing sugar in a huangjiu fermentation process.
Figure 3C:
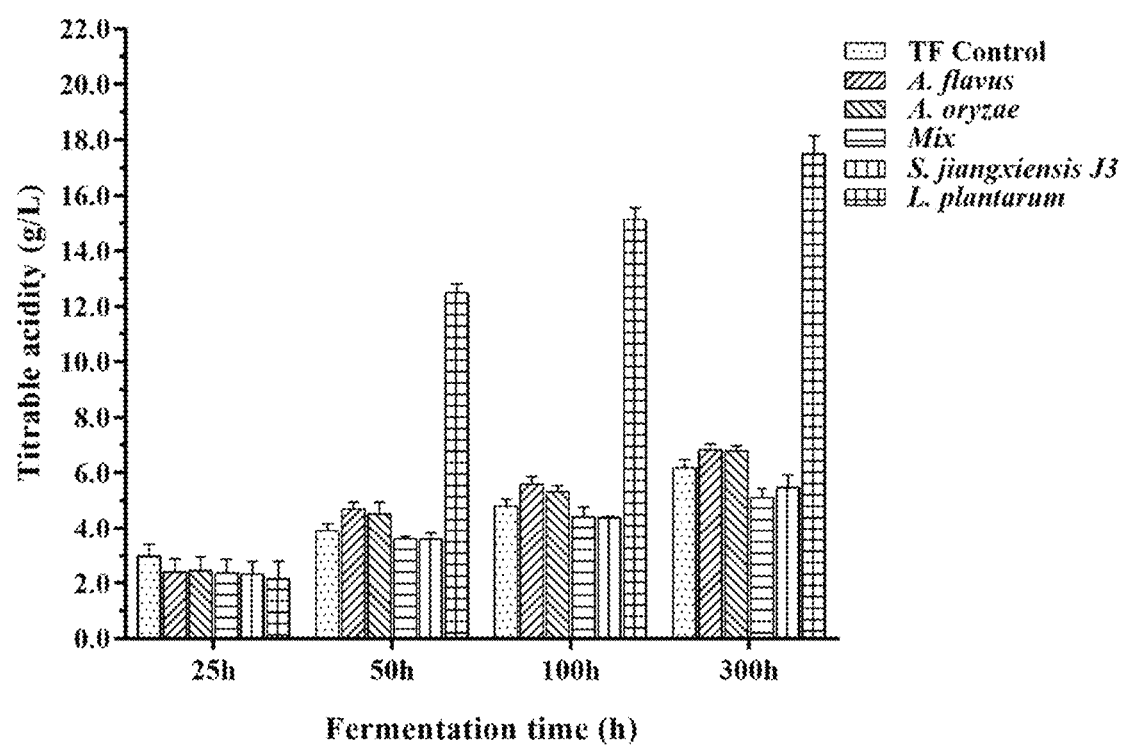
FIG. 3C is a change of a titratable acid in a huangjiu fermentation process.
Figure 3D:
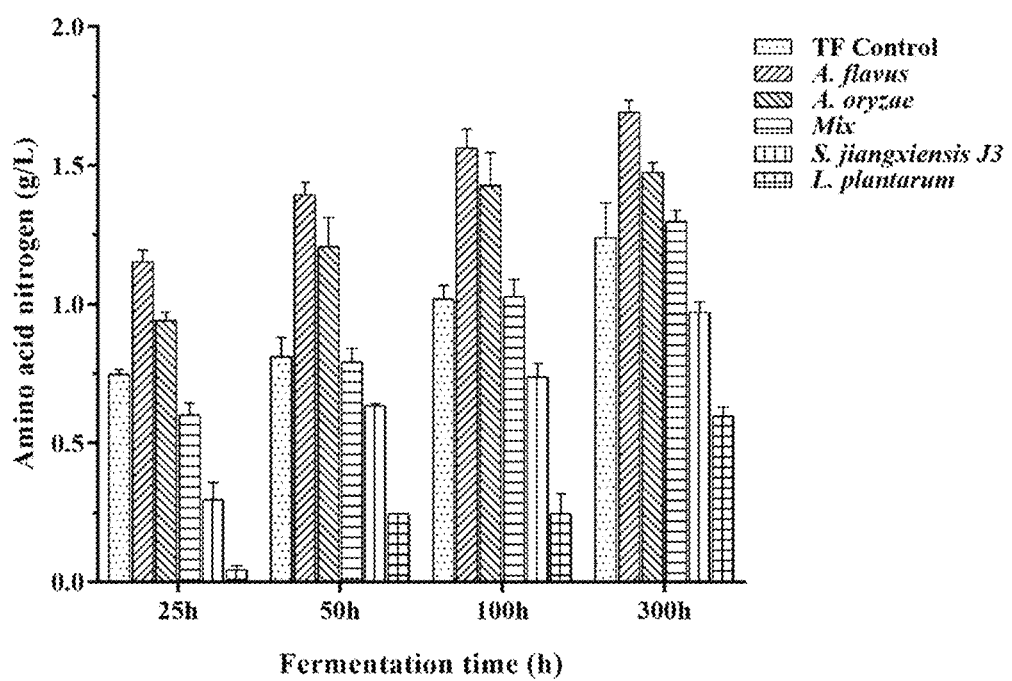
FIG. 3D is a change of amino acid nitrogen in a huangjiu fermentation process.

A PCR product was detected by 1% agarose gel electrophoresis and sent to a gene sequencing company for sequencing. According to returned sequencing results, BLAST sequence alignment was performed through an NCBI official website, BLAST alignment was performed with obtained 16S rDNA sequences, and phylogenetic analysis was performed. The results are as shown in FIGS. 1-2. A homology similarity of a nucleotide sequence (SEQ ID NO.1) of a strain J2 to that of *S. hirsuta* (GenBank accession numbers: MN515057.1 and NR_118870.1) was 98.30% or above, and the strain was named as the *Saccharopolyspora hirsuta* J2. A homology similarity of a nucleotide sequence (SEQ ID NO. 2) of a strain J3 to that of *S. jiangxiensis* (GenBank similar sequence number: MG255179.1) was 98.84% or more, and the strain was named as the *Saccharopolyspora jiangxiensis* J3.

(4) Analysis of Biogenic Amine Metabolism Capacity of *S. hirsuta* J2 Strain

Strain activation: The preserved *S. hirsuta* J2 was inoculated into the *Actinomycetes* liquid medium with an inoculum size of 10%, and cultured at 30° C. in a shaker for 48 h to obtain a primary seed solution. The activated strain was inoculated into the *Actinomycetes* liquid medium with an inoculum size of 10%, and cultured in a shaker at a rotation speed of 150 r/min and at temperature of 30° C. for 48 h.

Sample pretreatment: The strain was inoculated into a biogenic amine production detection medium and a biogenic amine degradation detection medium, and cultured at 28° C. in a shaker for 5 d, and centrifuged at 12000 r/min for 5 min and a supernatant was collected.

*Actinomycetes* liquid medium: Potassium nitrate 1.0 g/L, potassium dihydrogen phosphate 0.5 g/L, magnesium sulfate 0.5 g/L, ferrous sulfate 0.01 g/L, sodium chloride 0.5 g/L, and soluble starch 20.0 g/L; pH 7.2-7.4 (25° C.).

Biogenic amine production detection medium: L-tyrosine 0.4 g/L, L-histidine 1 g/L, L-lysine 1 g/L, L-ornithine 1 g/L and 5'-pyridoxal phosphate 0.05 g/L added into the *Actinomycetes* liquid medium.

Biogenic amine degradation detection medium: 50 mg/L of biogenic amine (including histamine, tyramine, cadaverine, putrescine, spermine, spermidine, tryptamine and β-phenylethylamine) was added into the *Actinomycetes* liquid medium, and pH was regulated to 6.0-6.2.

Analysis of biogenic amine-reducing effect of the *S. hirsuta* J2: The amount of the biogenic amines produced by the *S. hirsuta* J2 cultured in the biogenic amine production detection medium and the biogenic amine degradation detection medium was less than 2.5 mg/L, and the amount of the biogenic amines detected was very small, thus indicating that the biogenic amines were basically not detected, and therefore, it was considered that the biogenic amines were not produced. A degradation rate to the tyramine, a degradation rate to histamine, a degradation rate to putrescine, a degradation rate to cadaverine and a degradation rate to total biogenic amines by the *S. hirsuta* J2 reached 77.41%, 100%, 58.1%, 47.71% and 72.98%, respectively, thus indicating that the strain had good ability to reduce the biogenic amines.

(5) Analysis of Biogenic Amine Metabolism Ability of *S. jiangxiensis* J3

Analysis of biogenic amine-reducing effect of the *S. jiangxiensis* J3: The amount of various biogenic amines produced by the *S. jiangxiensis* J3 cultured in a medium where there were biogenic amine precursors was less than 2.5 mg/L, and the amount of the biogenic amines detected was very small, thus indicating that the biogenic amines are basically not detected, and therefore, it was considered that the biogenic amines were not produced. A degradation rate to tyramine, a degradation rate to histamine, a degradation rate to putrescine, a degradation rate to cadaverine, and a degradation rate to the total biogenic amines by the *S. jiangxiensis* J3 reached 81.55%, 100%, 51.8%, 40.01% and 69.09%, respectively, thus indicating that the strain had good ability to reduce the biogenic amines.

Example 2: Activation Culture of *Saccharopolyspora*

*Actinomycetes* liquid medium: Potassium nitrate 1.0 g/L, potassium dihydrogen phosphate 0.5 g/L, magnesium sulfate 0.5 g/L, ferrous sulfate 0.01 g/L, sodium chloride 0.5 g/L, and soluble starch 20.0 g/L; pH 7.2-7.4 (determined at 25° C.).

PDA medium: Potato powder 6.0 g/L, glucose 20.0 g/L, and agar 20.0 g/L; pH 5.4-5.8. The PDA medium was subjected to autoclaved sterilization at 121° C. for 15 min. A solid medium was added on this basis.

MRS medium: Beef extract 10 g/L, peptone 10 g/L, yeast extract 0.5 g/L, glucose 20 g/L, Tween-80 0.10 g/L, sodium acetate 5 g/L, dipotassium hydrogen phosphate 2 g/L, diammonium hydrogen citrate 2 g/L, magnesium sulfate 0.58 g/L and manganese sulfate 0.28 g/L.

The *S. hirsuta* J2 screened in Example 1 was inoculated into the *Actinomycetes* liquid medium, with an inoculum size of 10% and cultured in a shaker at 30° C. for 48 h to obtain a primary seed solution. The activated strain was inoculated into the *Actinomycetes* liquid medium, with an inoculum size of 10%, and cultured in a shaker at a rotation speed of 150 r/min and at temperature of 25 to 45° C. for 48 h to obtain a bacterial solution with a cell concentration of $10^5$-$10^6$ CFU/mL, and the bacterial solution was used for preparation of pure wheat koji after cultured to maturity.

Preserved *Aspergillus flavus* and *Aspergillus oryzae* were inoculated onto a PDA plate and cultured at 28° C. for 3-5 days. Then a spore solution was washed with sterile water, the washed spore solution was transferred into a PDA eggplant flask again, and cultured at 28° C. for 3-5 days to obtain a bacterial solution with a cell concentration of $10^5$-$10^6$ CFU/mL, and the bacterial solution was used for production of the pure wheat koji after spores were mature.

Preserved *Lactobacillus plantarum* (*L. plantarum*) was inoculated into the MRS medium, with an inoculum size of 10%, and subjected to anaerobic culture at constant temperature of 37° C. for 24 h to obtain a primary seed solution. The activated seed solution was inoculated again into the MRS liquid medium, with an inoculum size of 10%, and subjected to anaerobic culture at constant temperature of 37° C. for 24 h to obtain a bacterial solution with a cell concentration of $10^5$-$10^6$ CFU/mL, and after cultured to maturity, the strain was used for production of the pure wheat koji.

*S. jiangxiensis* J3 pure wheat koji was prepared according to the same method as described above, with a difference that the *S. hirsuta* J2 was replaced with the *S. jiangxiensis* J3.

Example 3: Preparation of *Saccharopolyspora* Pure Wheat Koji (1) Wheat grinding: A degree of crushing of wheat was 3-5 pieces per grain, with a small amount of powder, and a wheat grain structure was made to broken and starch was exposed.

(2) Wheat tempering: 35-40% of clear water was added into the material obtained after treatment in step (1), and stirring was performed for 20-25 min to make it fully and evenly absorb moisture.

(3) Cooking for sterilization: The material obtained after treatment in step (2) was sterilized at 121° C. for 30 min.

(4) Inoculation: After the material obtained in step (3) was cooled to 36° C., the strain activated according to the method of Example 2 was inoculated with a bacterial solution inoculum concentration of $10^5$-$10^6$ CFU/mL, and with an inoculum size of 5%0-15%.

(5) Proper sample temperature and room temperature were kept after a koji material entered a plate, and the koji material was subjected to static culture for about six hours.

a) In a spore germination period, 6 hours after the koji material entered a tray, the sample temperature slowly rose to about 34-35° C., an automatic control mode started small-air volume intermittent ventilation, for 5-10 minutes each time, at an interval of 2 hours, and the sample temperature was made to drop to 32° C., and it was required that the koji material was blown through evenly.

b) In a mycelium growth period, after 3-5 times of intermittent ventilation, mycelia started to grow, the sample temperature rose to 35° C. or above, the koji material started to agglomerate, and at this time, continuous ventilation should be performed to maintain the sample temperature at about 35° C.

c) In a mycelium propagation period, 12 hours after inoculation, the sample temperature rose rapidly, and at this time, koji turning should be performed depending on a first-time agglomeration situation. Before the koji turning, a temperature measurement probe was raised first, a koji turning machine was enabled, then the koji material was spread, and the temperature measurement probe was put down. A ventilation and spray system was enabled.

d) After the first-time koji turning, the sample temperature was kept between 36-37° C., ventilation and spraying were kept smooth, and about 20 hours later, the koji material agglomerated again, it was observed by naked eyes that the koji material looked white, the temperature was controlled at 37° C. or below, second-time koji turning was performed, and after the two times of koji turning, the sample temperature should be controlled at about 35° C.

(6) Koji was discharged: Culture was performed for 72-96 h; after the culture ended, the wheat koji was stored in a freezer at 4-7° C. for later use.

The *S. hirsuta* J2 pure wheat koji and the *S. jiangxiensis* J3 pure wheat koji each with a cell order of $10^{15}$ CFU/g were prepared according to the above method.

Example 4: Preparation of *Saccharopolyspora* Mixed Wheat Koji

The *S. hirsuta* J2 pure wheat koji and the *S. jiangxiensis* J3 pure wheat koji prepared in Example 3 were mixed in any ratio to prepare mixed wheat koji.

Optionally, the mixed wheat koji for fermentation of brewing alcoholic beverages is prepared by mixing the *S. hirsuta* J2 pure wheat koji and the *S. jiangxiensis* J3 pure wheat koji in a mass ratio of 1:(0.8-1.5).

Example 5: Application of *Saccharopolyspora* Pure Wheat Koji In Huangjiu Fermentation (1) A raw material ratio (by fermentation volume per liter) for conventional huangjiu fermentation that was selected in the example was shown as below:

Steamed rice: 500 g; clear water 417 L; and distiller's yeast: 38 g.

(2) A conventional huangjiu brewing process:

a) *Saccharomyces cerevisiae* activation culture: *Saccharomyces cerevisiae* in a glycerol preservation tube was transferred to a YPD medium on a sterile operating platform, and cultured at 30° C. and at 150 r/min for 24 h. Then the cultured *Saccharomyces cerevisiae* was transferred into prepared distiller's yeast. The transferred *Saccharomyces cerevisiae* was cultured at 30° C. and at 150 r/min for 18-24 h for later use.

b) Distiller's yeast preparation: 600 g of steamed rice was taken, 1600 mL of clear water, 60 g of raw wheat koji, and 800 U/g of glucoamylase were added for saccharification at saccharification temperature controlled at 55-65° C. for 3-4 hours. After saccharification ended, an appearance sugar degree was not less than 12° Bx, sterilization was performed at 115° C. for 15 min, cooling was performed to 24-31° C. after sterilization, 5% of the mature *Saccharomyces cerevisiae* seed solution was inoculated, culture temperature did not exceed 30° C., and culture time was 24 h, and the distiller's yeast was obtained after culture to maturity.

c) Material dropping and fermentation were performed according to the raw material ratio of the conventional huangjiu fermentation in step (1). In an experimental group, there was 45.3 g of pure wheat koji, and in a control group: there were 39.3 g of raw wheat koji, and 6.0 g of cooked wheat koji.

First 4 days belonged to a primary fermentation stage, temperature was controlled at 28-30° C., fermentation lasted for 4 days, rake-stirring was performed no less than once a day in the first 4 days, and first rake-stirring time is 8-10 h. At a secondary fermentation stage, temperature was 13-15° C., rake-stirring was performed once a day, and fermentation lasted for 10-15 d.

The control group (TF Control) was obtained by adjusting the pure wheat koji in c) in the example to 39.3 g/L of raw wheat koji and 6.0 g/L of cooked wheat koji that were sampled from a factory.

Example 6: Application of *Saccharopolyspora* Mixed Wheat Koji in Huangjiu Fermentation In a mixed wheat koji fermentation group, the mixed wheat koji of the *S. hirsuta* J2 pure wheat koji and *S. jiangxiensis* J3 pure wheat koji and *Saccharomyces cerevisiae* were employed for co-fermentation using a conventional brewing method.

In a mixed bacteria preparation group (Mix), the *S. hirsuta* J2 pure wheat koji and the *S. jiangxiensis* J3 pure wheat koji were added in a cell number ratio of 1:1, in total of 45.3 g.

experimental group added with the *S. hirsuta* J2 reached 6434.81±123.3 mg/L, and was increased by 40.37% in comparison with that in the control group. The amino acid content in an experimental group added with the Mix, the amino acid content in an experimental group added with the *A. flavus* and the amino acid content in an experimental group added with the *A. oryzae* were not much different, but were all significantly higher than that in the control group (TF Control). The total amino acid content in an experimental group added with the *S. jiangxiensis* J3 was not much different from that in the control group, and content of some amino acids was significantly higher than that in the control group.

TABLE 1

Analysis of Amino Acid Content of Fermented Huangjiu Samples

| mg/L | TF Control | *A. flavus* | *A. oryzae* | Mix | *S. jiangxiensis* J3 | *L. plantarum* |
|---|---|---|---|---|---|---|
| Asp | 172.94 ± 15.89 | 255 ± 14.24 | 333.26 ± 7.48 | 355.99 ± 72.02 | 199.4 ± 28.17 | 99.89 ± 7.78 |
| Glu | 516.86 ± 42.94 | 783.95 ± 12.37 | 866.45 ± 27.67 | 635.99 ± 106.59 | 498.28 ± 71.53 | 415.12 ± 32.04 |
| Asn | 123.95 ± 7.52 | 153.64 ± 30.65 | 184.51 ± 3.41 | 195.61 ± 49.55 | 111.75 ± 23.6 | 95.89 ± 8.05 |
| Ser | 67.66 ± 3.83 | 90.51 ± 18.2 | 274.78 ± 5.61 | 216.54 ± 32.15 | 101.12 ± 12.5 | 27.02 ± 7.15 |
| Gln | 315.06 ± 17.31 | 433.09 ± 15.19 | 438.03 ± 7.36 | 475.45 ± 103.7 | 299.04 ± 46.13 | 115.66 ± 47.26 |
| His | 80.01 ± 8.57 | 105.37 ± 10.58 | 121.28 ± 5.8 | 148.57 ± 51.83 | 62.81 ± 17.83 | 50.65 ± 18.85 |
| Gly | 169.7 ± 19.75 | 292.95 ± 5.67 | 374.39 ± 18.53 | 398.02 ± 44.28 | 240.61 ± 20.66 | 80.2 ± 10.89 |
| Thr | 101.18 ± 20.49 | 151.8 ± 6.19 | 131.38 ± 11.09 | 146.72 ± 42.94 | 55.69 ± 7.81 | 44.36 ± 4.78 |
| Arg | 313.12 ± 213.87 | 524.16 ± 184.11 | 412.13 ± 5.66 | 528.4 ± 178.2 | 384.33 ± 80.6 | 713.42 ± 74.24 |
| Aala | 327.06 ± 33.76 | 431.84 ± 22.42 | 553.68 ± 3.08 | 457.64 ± 161.32 | 423.41 ± 47.88 | 154.45 ± 7.95 |
| gaga | 86.89 ± 13.71 | 101.5 ± 3.53 | 117.58 ± 2.45 | 137.54 ± 26.05 | 151.08 ± 62.91 | 106.25 ± 15.86 |
| tyr | 346.68 ± 30.96 | 334.19 ± 45.55 | 490.71 ± 6 | 339.04 ± 74.18 | 297.97 ± 40.1 | 250.97 ± 13.44 |
| cys-s | 65.91 ± 2.07 | 101.36 ± 44.88 | 9.74 ± 1.71 | 26.19 ± 9.44 | 28.92 ± 14.23 | 25.28 ± 21.25 |
| val | 241.78 ± 9.77 | 334.94 ± 3.44 | 325.35 ± 2.51 | 263.89 ± 60.77 | 245.62 ± 33.19 | 143.27 ± 10.84 |
| met | 67.06 ± 0.63 | 102.32 ± 2.82 | 77.07 ± 1.76 | 54.86 ± 13.11 | 23.53 ± 2.76 | 41.15 ± 1.46 |
| trp | 101.26 ± 5.8 | 135.6 ± 5.44 | 139.43 ± 1.15 | 157.61 ± 26.34 | 111.35 ± 25.44 | 83.05 ± 4.56 |
| phe | 374.52 ± 10.99 | 495.37 ± 3.34 | 451.88 ± 2.66 | 302.39 ± 62 | 279.74 ± 37.17 | 277.99 ± 10.76 |
| ile | 179.49 ± 9.85 | 261.47 ± 10 | 290.16 ± 5.36 | 179.84 ± 18.62 | 149.25 ± 16.88 | 100.74 ± 7.66 |
| leu | 597.15 ± 12.93 | 836.29 ± 13.54 | 703.73 ± 6.12 | 509.94 ± 40.05 | 377.94 ± 42.1 | 339.71 ± 20.96 |
| lys | 302.76 ± 17.5 | 338.29 ± 16.8 | 275.44 ± 0.53 | 356.05 ± 97.92 | 208.68 ± 44.52 | 181.68 ± 26.3 |
| pro | 33.26 ± 20.14 | 43.72 ± 6.69 | 59 ± 9.81 | 135.02 ± 27.19 | 115.82 ± 27.26 | 128.42 ± 30.41 |
| Total | 4584.28 ± 105.28 | 6307.36 ± 322.13 | 6630 ± 101.19 | 6021.30 ± 117.92 | 4366.34 ± 567.73 | 3475.15 ± 227.53 |

Note:
gaga is γ-aminobutyric acid.

Changes in physical and chemical indexes in a huangjiu fermentation process: In order to further verify a function of the *Saccharopolyspora* in huangjiu fermentation, changes of physical and chemical indexes (alcoholic content, reducing sugar, titratable acid and amino acid nitrogen) in a fermentation process of conventional wheat koji and in a fermentation process of pure wheat koji were compared. There were 6 groups of pure fermentation in total, namely an *A. flavus* (commonly used bacteria in huangjiu fermentation) group, an *A. oryzae* (commonly used bacteria in Japanese sake brewing) group, an *S. jiangxiensis* J3 group, a Mix group and an *L. plantarum* group, and these 5 kinds of pure wheat koji each performed co-fermentation with the *Saccharomyces cerevisiae* using the conventional brewing method. By the end of the fermentation, except for the *L. plantarum* group, the alcoholic content, acidity and amino acid nitrogen content in each of the other groups all reached national standards for huangjiu (FIG. 3). Titratable acid content in the *L. plantarum* group was increased rapidly to 17.50 g/L, and samples showed obvious rancidity, thus indicating that the *Saccharopolyspora* had little effect on important physical and chemical indexes in the huangjiu fermentation process, and the fermentation was normal.

Amino acid content of fermented huangjiu samples: Amino acid content of fermented huangjiu was analyzed by employing an HPLC method. The amino acid content in an Analysis of biogenic amine-reducing effect of the *Saccharopolyspora*: The biogenic amine content of an obtained huangjiu product was detected using the high performance liquid chromatography. The biogenic amine content in a sample group added with the *S. hirsuta* J2 was reduced by 21.71% in comparison with that in the control group. The biogenic amine content in a sample group added with the *S. jiangxiensis* J3 was reduced by 35.09% in comparison with that in the control group. The biogenic amine content in a mixed bacteria preparation group (Mix group) added with the *S. hirsuta* J2 and the *S. jiangxiensis* J3 was reduced by 42.17% in comparison with that in the control group.

Figure 4:
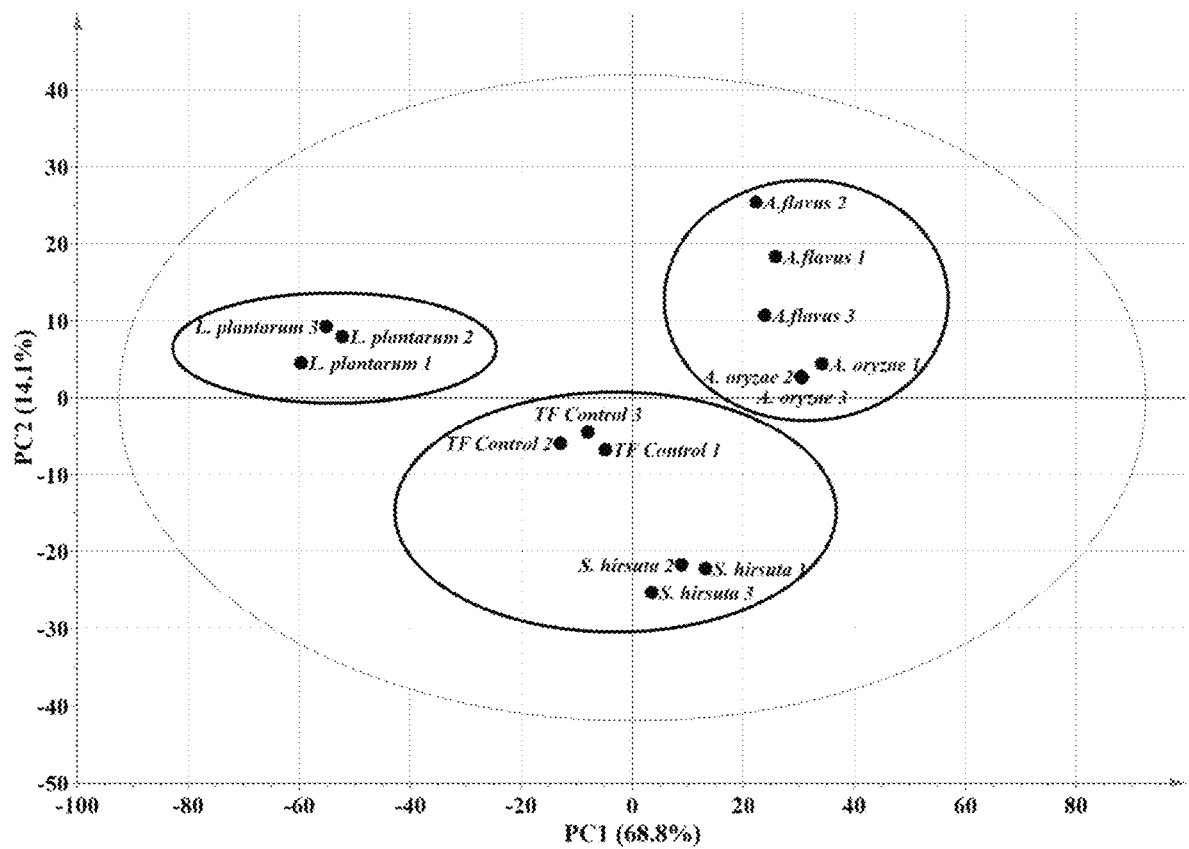
FIG. 4 is main component analysis of flavor substances of a *S. hirsuta* J2 fermented huangjiu sample.
Figure 5:
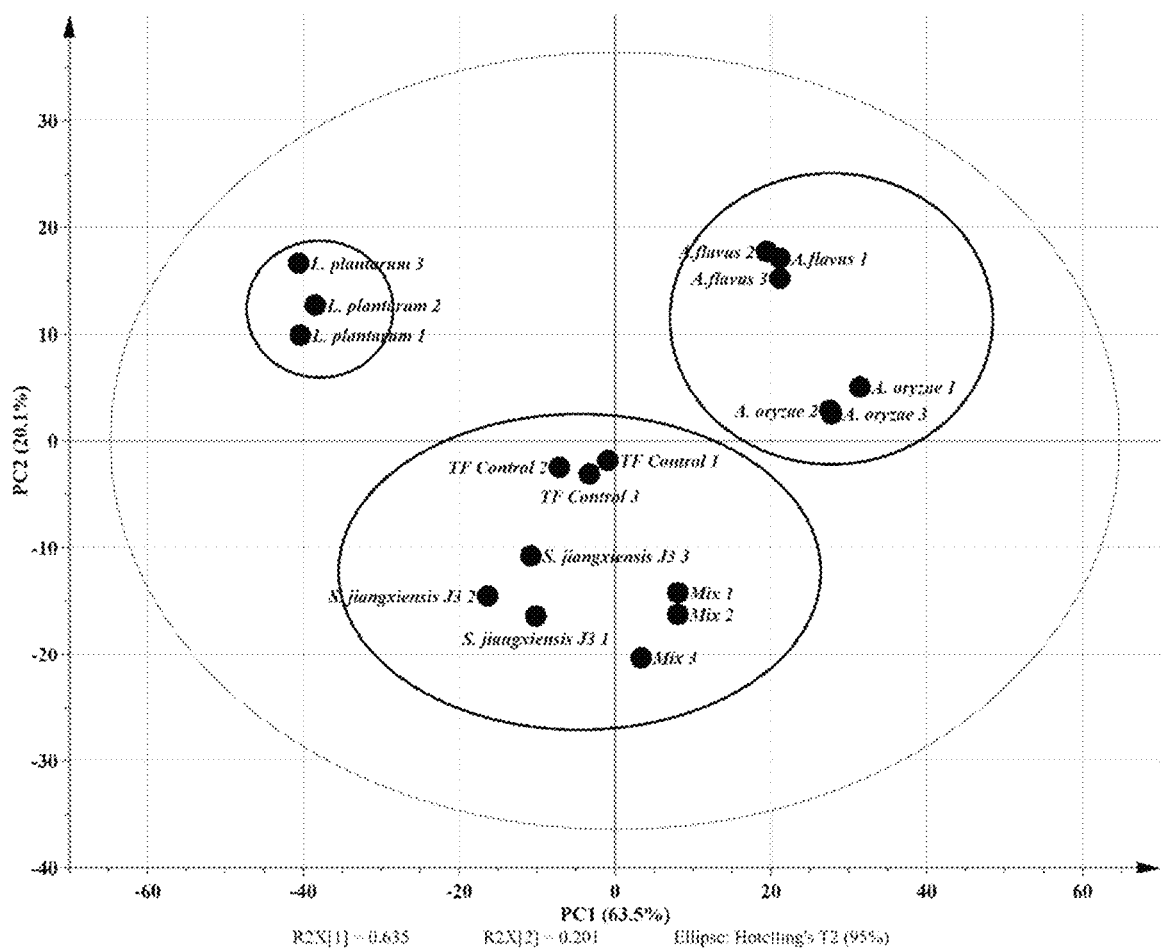
FIG. 5 is main component analysis of flavor substances of a *S. jiangxiensis* J3 fermented huangjiu sample.

Analysis of pure fermentation and conventional fermentation flavors: Changes and similarities of flavor components in pure and conventional fermentation samples were analyzed using a main component analysis method. Biplot analysis of all samples showed that cumulative variance contribution rates of first two main components in the huangjiu fermented with the *S. hirsuta* J2 and the *S. jiangxiensis* J3 were both 83.6%, which could explain a flavor difference of most fermented samples. It could be seen from FIG. 4 that a conventional fermentation group and the *S. jiangxiensis* J3 group stayed together, and were obviously separated from the *Aspergillus* (*A. flavus* and *A. oryzae*) groups and the *L. plantarum* group, thus indicating that the

*Saccharopolyspora* involved in synthesis of most flavor substances and played a leading role in huangjiu fermentation.

Example 7: Application of *Saccharopolyspora* Bacterium Agent in Huangjiu Fermentation Huangjiu fermentation was performed according to a conventional huangjiu dropped material formula in Example 5. There were a Mix group and a *S. Jiangxiensis* J3 group as experimental groups, with a difference that wheat koji inoculation proportions were both 10%, but the *S. Jiangxiensis* J3 pure wheat koji was inoculated in the *S. Jiangxiensis* J3 group, and a compound strain wheat koji prepared from the *S. Jiangxiensis* J3 and the *S. hirsuta* J2 according to the method in Example 3 was inoculated in the Mix group. A huangjiu brewing technology and an index determination method were carried out with reference to Example 4.

(1) Effect on Basic Physical and Chemical Indexes of Huangjiu

It could be seen from Table 2 that the alcoholic content of each group reached about 14% v/v after fermentation ended, and the reducing sugar content, the total acid content and the amino acid nitrogen content of all samples were each 4.52-5.03 g/L, which all met the physical and chemical requirements of the huangjiu. Significance analysis showed that the alcoholic content, the total acid content and the amino acid nitrogen content in the Mix group and *S. Jiangxiensis* J3 group were not significantly different from those in the control group (P>0.05), which indicating that inoculation of the *Saccharopolyspora* such as the *S. hirsuta* J2 and the *S. Jiangxiensis* J3 had little effect on the important physical and chemical indexes in the huangjiu fermentation process, and would not bring an adverse effect to the huangjiu fermentation process.

TABLE 2

Physical and Chemical Indexes of Huangjiu When Fermentation Ended

| Indexes | Control group | Mix group | *S. jiangxiensis* J3 group |
|---|---|---|---|
| Alcoholic content (% v/v; 20° C.) | 14.20 ± 0.60 | 14.20 ± 0.72 | 14.30 ± 0.50 |
| Reducing sugar content (g/L) | 20.02 ± 1.64 | 24.25 ± 0.23 | 9.45 ± 3.13 |
| Total acid content (g/L) | 4.68 ± 0.09 | 4.74 ± 0.26 | 4.81 ± 0.16 |
| Amino acid nitrogen content (g/L) | 0.82 ± 0.04 | 0.84 ± 0.06 | 0.82 ± 0.02 |

(2) Effect of *Saccharopolyspora* on Huangjiu Biogenic Amine Content

After the fermentation ended, the biogenic amine content of samples in the mixed bacteria preparation Mix group and the biogenic amine content of samples in the *S. Jiangxiensis* J3 group were 15.57±0.44 mg/L and 16.88±1.41 mg/L, respectively, which were lower than 26.75±2.39 mg/L in the control group. An average value of the total amine content of the *S. hirsuta* J2 was reduced by 41.79% in comparison with that in the control group, and an average value of the total amine content of the *S. Jiangxiensis* J3 group was reduced by 36.90% in comparison with that in the control group, thus indicating that the mixed bacteria preparation Mix and the *S. Jiangxiensis* J3 both had the effect of reducing the biogenic amine content.

In summary, the inoculation of the mixed bacteria preparation Mix and the *S. Jiangxiensis* J3 in a huangjiu fermentation system did not affect normal quality of the huangjiu, and degradation rates of total amines reached 41.79% and 36.90% in comparison with that in the control group, respectively, thus indicating that the mixed bacteria preparation Mix and the *S. Jiangxiensis* J3 both had a potential to be directly added in the production of the huangjiu and regulation of the biogenic amine content of the huangjiu, and the mixed bacteria preparation Mix had a better degradation effect on the biogenic amines in huangjiu.

Example 8: *S. hirsuta* J2 Applied to Fermented Sausage to Reduce Biogenic Amine Content (1) Activation Culture of Strain

*Actinomycetes* liquid medium: Potassium nitrate 1.0 g/L, potassium dihydrogen phosphate 0.5 g/L, magnesium sulfate 0.5 g/L, ferrous sulfate 0.01 g/L, sodium chloride 0.5 g/L, and soluble starch 20.0 g/L; pH 7.2-7.4 (determined at 25° C.).

The preserved *S. hirsuta* J2 was inoculated into the *Actinomycetes* liquid medium, with an inoculum size of 10%, and cultured in a shaker at 30° C. for 59 h to obtain a primary seed solution. The activated strain was inoculated into the *Actinomycetes* liquid medium, with an inoculum size of 10%, and cultured in a shaker for 48 h, at a rotation speed of 150 r/min, and at temperature of 30° C., and the cultured activated strain was used for sausage fermentation after cultured to the cell order of $10^5$-$10^7$ CFU/mL.

(2) Preparation of Fermented Sausage

By mass, 65-80% of lean and 20-35% of fat were taken. The lean and the fat were washed, and bones, tendons, sarcolemmas, lymphatics, blood vessels, lesions and injured parts were removed. The fat and the lean were separated and cut into 4-5 cm meat pieces. The lean and about 5-8% of ice chips were put into a chopper for chopping for 1-3 min. Based on pork mass, 0.01-0.15% of sodium nitrite, 2-3% of salt, 0.2-0.3% of composite phosphate, and 0.05-0.06% of sodium ascorbate were added. Spices, pepper, garlic, chili, and nutmegs were 0.2%-0.3% of the raw meat. Two groups were inoculated with 8-12% of activated *Saccharopolyspora*, separately, and the other group was not inoculated, as a control, chopping was performed for 1-2 min, and then the fat and about 5-8% of ice chips were added, and chopped for 4-6 min. The mixture was filled into a casing after curing. Sausage fermentation process parameters are as shown in Table 3.

TABLE 3

| Sausage Fermentation Process Parameters | | | |
|---|---|---|---|
| Processing procedures | Temperature/° C. | Time | Relative humidity/% |
| Curing | 4 | 12 h | — |
| Fermentation | 30 | Time required for pH value to drop to 5.1 | 90 |
| Maturing 0 d | 14-16 | 1 d | 75-80 |
| Maturing 1 d | 14-16 | 1 d | 70-75 |
| Maturing 2-10 d | 14-16 | 9 d | 65-70 |

(3) Analysis of Biogenic Amine-Reducing Effect of *S. hirsuta* J2

Strain activation and determination of biogenic amine content were performed with the method in Example 1.

Sample preparation method: 5.0 g of minced sample was weighed and placed into a 50 mL centrifuge tube, 20 mL of 5% trichloroacetic acid was added and ultrasonic treatment was performed for 30 min. The treated minced sample was transferred to a 50 mL centrifuge tube with a plug, and centrifuged at 6,000 r/min for 10 min, a supernatant was transferred to a 50 mL volumetric flask, residues were extracted with 20 mL of the solution one more time, and the supernatants were combined and diluted to scale.

It could be seen from table 4 that the pH of a sausage fermented with the *S. hirsuta* J2 after the sausage was fermented to maturity was 6.16±0.16 separately, while the pH in the control group was 6.51±0.17, and there was no significant difference in terms of moisture content and crude protein content. The average content of biogenic amines in the sausage fermented with the *S. hirsuta* J2 after maturation was 129.60 mg/kg, which was reduced by 36.19% in comparison with that in the control group.

TABLE 4

Fermented matured sausage indexes

| Indexes | Control group | *S. hirsuta* J2 |
| --- | --- | --- |
| pH value | 6.51 ± 0.17 | 6.16 ± 0.16 |
| Moisture | 62.56 ± 7.04 | 67.66 ± 2.68 |
| Crude protein | 59.66 ± 3.17 | 59.31 ± 6.75 |
| Biogenic amine | 229.03 ± 12.00 | 129.60 ± 7.10 |

Example 9: *S. hirsuta* J2 Applied to Baijiu to Reduce Biogenic Amine Content Preparation of *Saccharopolyspora* pure wheat koji used in baijiu brewing referred to a wheat koji preparation method in Example 3. The biogenic amine content was determined with the method in Example 1.

Two rounds of fermentation were used as the brewing method. During the first round of fermentation, the sorghum was steamed, and then subjected to air cooling to 28° C. 4% of an *Aspergillus oryzae* seed solution was added and the mixture was cultured at 28° C. for 24 h. 10% of rice husk, 15% of Daqu, 8% of bran and 5-9% of pure wheat koji were added, and a *Saccharomyces cerevisiae* seed solution was inoculated in a proportion of 1%, then sealing was performed, and distilling was performed after 30 days of fermentation. In a second round of fermentation, 10% of medium-temperature Daqu was added, and the *Saccharomyces cerevisiae* seed solution was inoculated in a proportion of 1%, with a concentration of $10^{10}40^{12}$ CFU/mL, and distilling was performed after further fermentation for 12-15 days.

Analysis of biogenic amine-reducing effect of *S. hirsuta* J2: The distilled baijiu was blended to alcoholic content 60% (V/V), the biogenic amine content of a blended sample was detected, and the biogenic amine content in a sample group added with the *S. hirsuta* J2 was reduced by 24.32% in comparison with that in the control group.

Example 10: *S. hirsuta* J2 Applied to Soy Sauce to Reduce Biogenic Amine Content Strain activation and determination of biogenic amine content were performed with the method in Example 1. Soy sauce was brewed by employing a high saline diluting method:

(1) Firstly, soybean meal and wheat were mixed in a ratio of 1:1, and then steamed;

(2) A *S. hirsuta* J2 seed solution with a cell concentration of $10^5$-$10^6$ CFU/mL was added in a ratio of 5%0-10%, and then salt water about 1.5-2 times the material mass was added; final salt content of soy sauce mash was about 18%, and water content was 65%, and then the well mixing was performed.

(3) Soy sauce culture fermentation: Initial fermentation temperature was controlled at 14-16° C., and the temperature gradually rose to about 35° C. as the fermentation progressed. The fermentation lasted for about 5 months.

(4) After completing fermentation, the soy sauce mash was pressed through a plate-and-frame filter to remove the soy sauce culture. After the pressing was finished, diatomaceous earth filtration and membrane filtration were carried out to remove the precipitate. The filtered clarified soy sauce was filled after being subjected to pasteurization.

Analysis of biogenic amine-reducing effect of *S. hirsuta* J2: The biogenic amine content of a soy sauce product added with the *S. hirsuta* J2 was reduced by 34.28% in comparison with that in the control group.

Example 11: *S. hirsuta* J2 Applied Cooking Wine to Reduce Biogenic Amine Content The pure fermented huangjiu was obtained according to the brewing method in Example 5. 10% of salt by mass was added into the fermented huangjiu. The fermented huangjiu was sterilized through a sterilizer at 85° C. for 30 min and subjected to hot filling.

Analysis of effect of strain on reducing biogenic amine content of cooking wine: The biogenic amine content of the cooking wine was detected using the HPLC, and the biogenic amine content of the sample group added with the *S. hirsuta* J2 was reduced in comparison with that in the control group.

Example 12: *S. hirsuta* J2 Used for Vinegar to Reduce Biogenic Amine Content The pure fermented huangjiu was obtained according to the brewing method in Example 5, to serve as a raw material for acetic fermentation. The biogenic amine content was determined with the method in Example 1.

The solid-state fermentation process was used for acetic fermentation. The Chinese crude bran, bran and Chinese rice wine were mixed well in a mass ratio of 1:4:10, and 5% of vinegar culture was inoculated. The culture was turned from the surface of the material every day for first 2 days after inoculation. The maintained temperature was 35-42° C. On days 6-8, the culture was turned to the bottom of the material. On days 8-12, the culture was turned from the bottom every day and the temperature was naturally lowered. The raw vinegar was separated from the vinegar culture and aged for 12 months after being sterilized at 85° C. for 30 min. The obtained product was subjected to high temperature sterilization before hot filling.

Quality of prepared vinegar was determined, and acetic acid content of the obtained solid-state fermented brewed vinegar was 55 g/L. The biogenic amine content of the vinegar was analyzed: the biogenic amine content of the vinegar was detected by the HPLC. The biogenic amine content in the sample group added with the *S. hirsuta* J2 was reduced in comparison with that in the control group.

Example 13: *S. hirsuta* J2 Used for Cheese Fermentation to Reduce Biogenic Amine Content Strain activation and determination of biogenic amine content were performed with the method in Example 1.

After fresh milk was homogenized and pasteurized, and cooled to room temperature, 0.1 g/L starter was added. Well mixing was performed. After acidification at 32-35° C. for 30 min, 0.05 g/L chymosin was added. Well mixing was performed, and after being formed, a curd was cut, and whey was drained to obtain a cheese curd. $10^5$-$10^6$ CFU/mL S. hirsuta J2 was sprayed on a surface of the cheese curd, and cultured at 30-37° C. for 3-5 d, and when it grew to maturity, 3.0 g/L salt was added, and then pressing forming was performed to obtain a cheese finished product.

The fermented cheese finished product was determined, and biogenic amine content of the cheese finished product added with the S. hirsuta J2 was reduced by 16.37% in comparison with that in the control group.

Example 14: S. hirsuta J2 Used in Cigarette Fermentation to Improve Quality and Reduce Harm Strain activation was performed with the method in Example 1. An activated bacterial solution was centrifuged at 4° C. and at 10,000 g for 15 min, and $10^5$-$10^6$ CFU/mL S. hirsuta J2 bacterial solution was prepared from collected bacterial cells with sterile water, and the bacterial solution was evenly sprayed on the surface of tobacco and fully mixed well. Taking treatment with a same amount of sterile water as a control, the tobacco was placed in a constant temperature and humidity box at 30-37° C. and humidity of 70-80% for 15 d of fermentation culture, ventilation was performed every day, and the tobacco was dried after the culture was over until moisture content was less than 15%.

Quality of the fermented tobacco was determined. An aroma component of the fermented tobacco was significantly increased, an offensive odor was reduced, and irritation was weakened. Harmful component content, i.e. tar content, HCN content, phenol content, $NH_3$ content and nitrite content, in the fermented tobacco, was reduced by 23.51%, 16.25%, 19.75%, 27.09% and 37.62%, respectively in comparison with those in the control group.

Example 15: S. Hirsuta J2 Used in Feed Fermentation to Increase Nutrient Conversion Rate Strain activation was performed with the method in Example 1. Rice bran, straw and soybean meal were mixed well in a ratio of (1-5):(1-5):2, and crushed to prepare a fermented material. Water was added in a material-water ratio of 1:(0.5-0.9), the S. hirsuta J2 with a cell concentration of $10^5$-$10^6$ CFU/mL was inoculated in a ratio of 10%0-10%, well mixing was performed, and the mixture naturally fermented at fermentation temperature of 30-40° C. for 4-9 d. After the fermentation ended, drying was carried out until water content was less than 15%, to obtain bio-fermented feed.

Analysis of quality of fermented feed: The obtained fermented feed had a special aroma, and was rich in nutrition and balanced in amino acid. Organic acid content, amino acid content and crude protein content of the fermented feed were increased by 26.77%, 21.98% and 18.53%, respectively in comparison with those in the control group.

Example 16: Saccharopolyspora Used to Reduce Biogenic Amine Content in Fermented Fish Strain activation was performed with the method in Example 1. A S. hirsuta J2 bacterial solution and a S. Jiangxiensis J3 bacterial solution were prepared, and mixed in a ratio of 1:(0.7-1.5) to obtain a mixed bacterial solution Mix.

A stinky mandarin fish was fermented with neutral protease, and a specific process was as follows:

(1) Sample pretreatment: A mandarin fish was gutted and weighed 3 kg.

(2) Fermentation broth preparation: Equal mass of drinking water as the mandarin fish was taken 100%, and based on this, 6% of salt, 1% of green Chinese onion, 0.6% of ginger, 0.1% of star anise, 0.05% of fennel, 0.05% of cumin, 0.01% of chili, 0.01% of Sichuan pepper, 300,000U neutral protease were added, and mixed well to obtain fermentation broth.

(3) Inoculation: The fermentation broth was divided into three portions, one portion of fermentation broth was inoculated with the mixed bacterial solution Mix with a cell concentration of $10^7$ CFU/mL, with an inoculum size of 10%, another portion of fermentation broth was inoculated with the S. jiangxiensis J3 with a cell concentration of $10^7$ CFU/mL, with an inoculum size of 10%, and the remaining portion of fermentation broth was not inoculated.

(4) Fermentation: The mandarin fish was immersed into the inoculated fermentation broth in step (3), a top layer was compacted with stones, and fermentation lasted at 20° C. for 6 days to obtain the stinky mandarin fish.

Determination method of biogenic amines: 5.0 g of minced fish flesh sample was weighed and placed into a 50 mL centrifuge tube. 20 mL of 5% trichloroacetic acid was added and ultrasonic treatment was performed for 30 min. Then the sample was transferred into a 50 mL centrifuge tube with a plug, and centrifuged at 6,000 r/min for 10 min. A supernatant was transferred into a 50 mL volumetric flask, and residues were extracted with 20 mL of the above solution one more time. The supernatants were combined and diluted to scale. Then 1 mL of supernatant was accurately measured and placed into a 15 mL centrifuge tube. 1 mL of a saturated $NaHCO_3$ solution was added. Well mixing was performed. 2 mL of dansyl chloride (5 mg/mL acetone) reagent was added. After well mixing, the mixture was placed in a 65° C. thermostat water bath for dark derivation for 30 min. After standing at room temperature, 0.5 mL of a saturated NaCl solution was added. After well mixing, 5 mL of ethyl ether was added. Vortex shaking was carried out for 20 s. After standing for stratification, an upper organic phase was transferred into a 15 mL centrifuge tube, a lower aqueous phase was extracted once again, two extracts were combined, and blow-dying with nitrogen was performed in a 50° C. water bath.

1 mL of acetonitrile was added and shaken and mixed well to dissolve residues. The dissolved solution passed through a 0.22 μm filter membrane. Determination was performed by the high performance liquid chromatography (HPLC).

After the fermentation ended, the biogenic amine of the stinky mandarin fish augmented with the mixed bacteria preparation Mix was reduced by 20.87% in comparison with those in the control group.

Example 17: Saccharopolyspora Used in Cooking Wine to Reduce Biogenic Amine Content The biogenic amine content was determined with the method in Example 1.

The pure fermented huangjiu was obtained according to the brewing method in Example 5. 10% of salt by mass was added into the fermented huangjiu. The fermented huangjiu was sterilized through a sterilizer at 85° C. for 30 min and subjected to hot filling.

Analysis of effects of strains on reducing biogenic amines in cooking wine: The biogenic amine content of the cooking wine was detected using the HPLC. The biogenic amine content in the sample group added with the mixed bacteria preparation Mix and the biogenic amine content in the sample group added with the *S. jiangxiensis* J3 were reduced by 23.16% and 18.91%, respectively in comparison with that in the control group.

Example 18: *Saccharopolyspora* Used in Vinegar to Reduce Biogenic Amine Content The pure fermented huangjiu was obtained according to the brewing method in Example 5, to serve as a raw material for acetic fermentation. The biogenic amine content was determined with the method in Example 1.

The solid-state fermentation process was used for acetic fermentation. The Chinese crude bran, bran and Chinese rice wine were mixed well in a mass ratio of 1:4:10, and 5% of vinegar culture was inoculated. The culture was turned from the surface of the material every day for first 2 days after inoculation. The maintained temperature was 35-42° C. On days 6-8, the culture was turned to the bottom of the material. On days 8-12, the culture was turned from the bottom every day and the temperature was naturally lowered. The raw vinegar was separated from the vinegar culture and aged for 12 months after being sterilized at 85° C. for 30 min. The obtained product was subjected to high temperature sterilization before hot filling.

Analysis of biogenic amine-reducing effect of mixed bacteria preparation Mix and *S. jiangxiensis* J3: The acetic acid content in the obtained solid-state fermented brewed vinegar was 55 g/L. The biogenic amine content of the samples was detected, and the biogenic amine content in the sample group added with the mixed bacteria preparation Mix and the biogenic amine content in the sample group added with the *S. jiangxiensis* J3 were reduced by 25.08% and 27.61%, respectively in comparison with that in the control group.

Example 19: *Saccharopolyspora* Used in Cheese Fermentation to Reduce Biogenic Amine Content Strain activation and determination of biogenic amine content were performed with the method in Example 1. The *S. hirsuta* J2 bacterial solution and the *S. Jiangxiensis* J3 bacterial solution were prepared, and mixed in a ratio of 1:(0.8-1.4) to obtain a mixed bacterial solution Mix.

After fresh milk was homogenized and pasteurized, and cooled to room temperature, 0.1 mL/L mixed bacterial solution of *Lactobacillus bulgaricus* and *Lactobacillus plantarum* in a cell number ratio of 1:1 was added as a starter (a cell concentration of the bacterial solution was $1 \times 10^8$-$10^9$ CFU/mL). Well mixing was performed. 0.05 g/L chymosin was added after acidification at 32-35° C. for 30 min. Well mixing was performed. After being formed, a curd was cut and whey was drained to obtain a cheese curd. $10^5$-$10^6$ CFU/mL *Saccharopolyspora* bacteria preparation was sprayed on the surface of the cheese curd. The cheese curd was placed at 30-37° C. for culture for 3-5 d, after it grew to maturity, 3.0 g/L salt was added, and then pressing forming was performed to obtain cheese finished products.

The fermented cheese finished products were determined. The biogenic amine content of cheese finished products added with the *S. jiangxiensis* J3 and the biogenic amine content of cheese finished products added with the mixed bacteria preparation were reduced by 13.33% and 21.66%, respectively in comparison with that in the control group.

Example 20: *Saccharopolyspora* Used in Cigarette Fermentation to Improve Quality and Reduce Harm Strain activation was performed with the method in Example 1. A *S. hirsuta* J2 bacterial solution and a *S. Jiangxiensis* J3 bacterial solution were prepared, and mixed in a ratio of 1:(0.7-1.5) to obtain a mixed bacterial solution Mix.

The activated bacterial solution was centrifuged at 4° C. and at 10,000 g for 15 min. $10^5$-$10^6$ CFU/mL bacterial solution was prepared from collected bacterial cells with sterile water. The bacterial solution was sprayed evenly on a surface of tobacco and fully mixed well. Taking treatment with the equal amount of sterile water as a control, and the tobacco was placed in a constant temperature and humidity cabinet at 30-37° C. and humidity of 70-80% for 15 d of fermentation culture. Ventilation was performed every day. After the culture, the tobacco was dried until moisture content was less than 15%.

Quality of the fermented tobacco was determined, and an aroma component of the fermented tobacco was significantly increased, an offensive odor was reduced, and irritation was weakened. Harmful component content, i.e. tar content, HCN content, phenol content, $NH_3$ content and nitrite content in the fermented tobacco fermented with the *S. jiangxiensis* J3 was reduced by 32.65%, 17.55%, 17.69%, 25.36% and 29.17%, respectively in comparison with those in the control group. Harmful component content, i.e. tar content, HCN content, phenol content, $NH_3$ content and nitrite content in tobacco fermented with the mixed bacteria preparation Mix was reduced by 30.12%, 17.14%, 22.01%, 16.73% and 27.15% respectively in compared with those in the control group.

Example 21: *Saccharopolyspora* Used in Feed Fermentation to Increase Nutrient Conversion Rate Strain activation was performed with the method in Example 1. A *S. hirsuta* J2 bacterial solution and a *S. Jiangxiensis* J3 bacterial solution were prepared, and mixed in a ratio of 1:(0.5-1.2) to obtain a mixed bacterial solution Mix.

Rice bran, straw and soybean meal were mixed well in a ratio of (1-5):(1-5):2, and crushed to prepare a fermented material. Water was added in a material-water ratio of 1:(0.5-0.9). The bacterial solution with a cell concentration of $10^5$-$10^6$ CFU/mL was inoculated in a ratio of 10%0-10%. Well mixing was performed, and the mixture naturally fermented at fermentation temperature of 30-40° C. for 4-9 d. After the fermentation ended, drying was performed until water content was less than 15%, to obtain bio-fermented feed.

Analysis of quality of fermented feed: The fermented feed obtained had a special aroma, and was rich in nutrition and balanced in amino acid. Organic acid content, amino acid content, and crude protein content of the fermented feed added with the *S. jiangxiensis* J3 were increased by 37.26%, 18.57%, 23.41%, respectively in comparison with those in the control group. Organic acid content, amino acid content, and crude protein content of the fermented tobacco fermented with the mixed bacteria preparation Mix were increased by 29.18%, 10.22% and 14.48%, respectively in comparison with those in the control group.

Although the disclosure has been disclosed as above in the preferred examples, it is not intended to limit the disclosure. Any person skilled in the art can make various changes and modifications without departing from the spirit and scope of the disclosure. Therefore, the protection scope of the disclosure should be as defined in the claims.

What is claimed is:

1. A method for reducing the content of biogenic amines during fermentation of foods, beverages, or condiments, which comprises:

culturing *Saccharopolyspora hirsuta* J2 with wheat koji, bran koji, Chinese yeast, or other types of koji, wherein the *S. hirsuta* J2 was deposited at the China Center for Type Culture Collection on Apr. 30, 2020, with a preservation number of CCTCC NO: M 2020103, and wherein *S. hirsuta* J2 is cultured in a medium to form an active microbial preparation with at least a $1 \times 10^5$ to $1 \times 10^7$ CFU per milliliter, adding the active microbial preparation to raw materials of foods, beverages, or condiments before fermenting the foods, beverages, or condiments, at an inoculum size of at least 10% (m/m), and fermenting the foods, beverages, or condiments with the active microbial preparation, thereby reducing the biogenic amines present in the fermented foods, beverages, or condiments, wherein the *S. hirsuta* J2 is cultured with wheat koji, bran koji, Chinese yeast, or other types of koji by:

(i) crushing raw materials for koji preparation,
(ii) stirring the crushed raw materials with water,
(iii) sterilizing the stirred raw materials, (iv) adding, in a sterile environment, the *S. hirsuta* J2 to the wheat koji, bran koji, Chinese yeast, or other types of koji, and (v) culturing the added *S. hirsuta* J2 at 25° C. to 55° C. for 72 hours to 96 hours, wherein the fermented beverage comprises fermented huangjiu or baijiu; and the fermented condiment comprises fermented vinegar, or soy sauce, and wherein the biological amine comprises one or more of tyramine, histamine, putrescine, and cadaverine.

2. The method according to claim 1, wherein the number of the *S. hirsuta* J2 per gram or per milliliter of the microbial preparation is greater than or equal to $1 \times 10^6$ CFU.

3. The method according to claim 1, wherein culturing further comprises culturing *Saccharopolyspora jiangxiensis* (*S. jiangxiensis*) J3 with the *S. hirsuta* J2, wherein the *S. jiangxiensis* J3 was deposited in the China Center for Type Culture Collection on Apr. 30, 2020, with a preservation number CCTCC NO: M 2020104, and wherein the active microbial preparation comprises both *S. hirsuta* J2 and *S. jiangxiensis* J3.

4. The method according to claim 3, wherein a cell number ratio of the *S. hirsuta* J2 to the *S. Jiangxiensis* J3 in the composition is 1: (0.8-1.2).

5. The method according to claim 4, wherein the number of the *S. hirsuta* J2 and *S. Jiangxiensis* J3 per gram or per milliliter of the composition is greater than or equal to $1 \times 10^6$ CFU.

6. The method according to claim 1, wherein the fermented food comprises a fermented cheese or sausage.

7. The method of claim 1, wherein the fermented beverage is wine, rice wine, or huangjiu.

8. Wheat koji, bran koji, Chinese yeast or other types of koji containing *Saccharopolyspora hirsuta* J2 and *Saccharopolyspora jiangxiensis* J3, wherein the *S. hirsuta* J2 was deposited in the China Center for Type Culture Collection on Apr. 30, 2020, with a preservation number CCTCC NO: M 2020103, and the *S. jiangxiensis* J3 was deposited in the China Center for Type Culture Collection on Apr. 30, 2020, with a preservation number CCTCC NO: M 2020104.

9. The wheat koji, bran koji, Chinese yeast or other types of koji according to claim 8, wherein raw materials for koji preparation are crushed, wherein the crushed raw materials are stirred with water, the stirred raw materials are sterilized, wherein the *S. hirsuta* J2 and *S. Jiangxiensis* J3 is added in a sterile environment, and wherein the added *S. hirsuta* J2 and *S. Jiangxiensis* J3 are cultured at 25° C. to 55° C. for 72 hours to 96 hours.

* * * * *